United States Patent [19]

Howard

[11] 4,098,126
[45] Jul. 4, 1978

[54] NON-DESTRUCTIVE TESTING OF PIPELINE

[75] Inventor: David Campbell Howard, Fritchley, England

[73] Assignee: British Gas Corporation, England

[21] Appl. No.: 784,614

[22] Filed: Apr. 4, 1977

[51] Int. Cl.² .............................................. G01B 5/28
[52] U.S. Cl. ................... 73/432 R; 33/178 F
[58] Field of Search ............ 73/432 R; 33/125 R, 33/178 E, 178 F, 141 G

[56] References Cited

U.S. PATENT DOCUMENTS

| 2,896,332 | 7/1959 | Elston et al. ........................ 33/178 F |
| 3,495,546 | 2/1970 | Brown et al. ................... 73/432 R X |
| 3,755,908 | 9/1973 | Ver Nooy ........................... 33/178 F |
| 3,940,855 | 3/1976 | Ver Nooy et al. ............ 33/178 F X |
| 3,973,441 | 8/1976 | Porter ................................. 73/432 R |

Primary Examiner—Richard C. Queisser
Assistant Examiner—Joseph W. Roskos
Attorney, Agent, or Firm—Watson, Cole, Grindle & Watson

[57] ABSTRACT

This invention relates to non-destructive testing of metallic pipelines using a pig having a novel way of mounting sensors for detecting any defect in the pipe wall. The sensors are mounted around the outer edge of an elastomeric cup which is rigidly fixed to the pig body. The sensors are maintained in contact with the internal surface of the pipe by a spring member which urges the sensors radially outward from the pig body.

5 Claims, 4 Drawing Figures

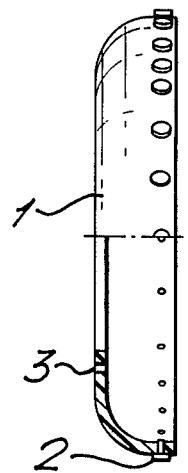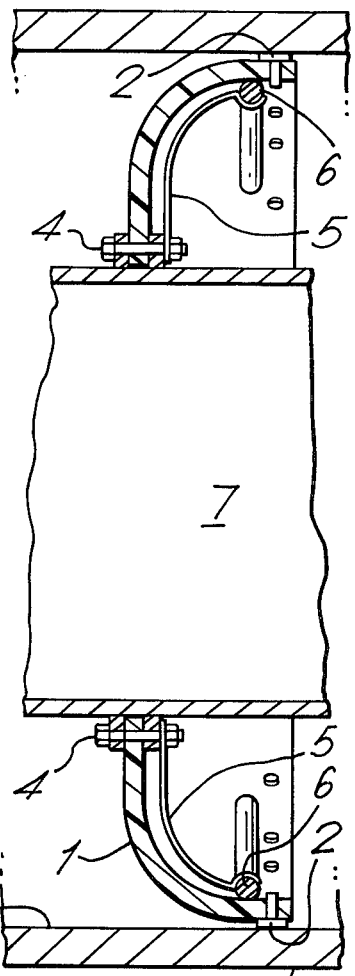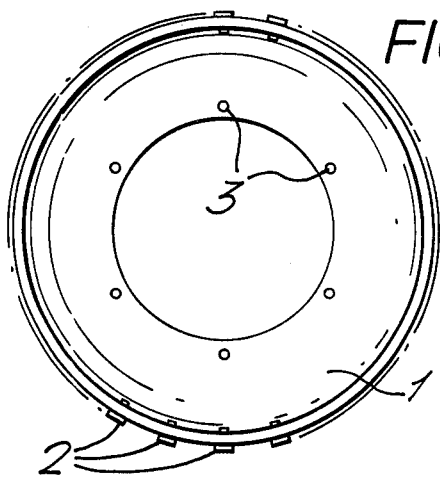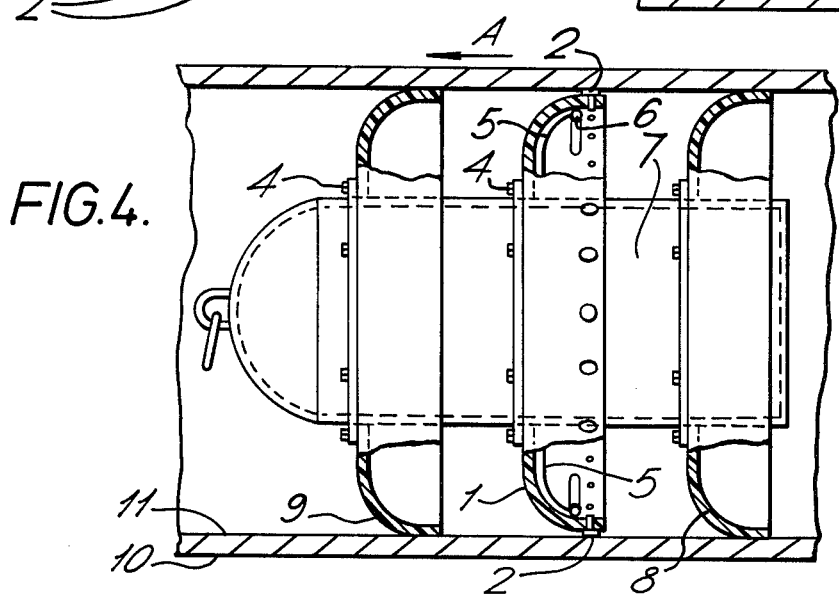

NON-DESTRUCTIVE TESTING OF PIPELINE

This invention relates to the non-destructive testing of metallic pipelines and, in particular, to apparatus for the in situ detection of corrosion and other faults.

It is the practice, from time to time, to clean the inner surface of the walls of pipelines used for the bulk transport of fluids. Cleaning is carried out by means of apparatus known as a pig which may be forced along the pipeline by means of gas or liquid pressure. The pig substantially fills the pipe cross-section and during the traverse scours the inner surface, removing debris previously deposited by the transported fluids.

Metallic pipes are subject to corrosion, internally by transported chemicals and externally by chemicals from the soil. It is therefore necessary to make periodic checks to determine the necessity for maintenance. In our co-pending British Patent Application No's 42162/75 and 3763/76 we describe methods of testing pipelines using sensing probes mounted on pigs. In one case the pig incorporates a powerful magnet with pole pieces mounted adjacent to the pipeline wall. Magnetisation is induced in the pipe thereby and is measured by means of coils, magneto-doides or Hall probes, and variations of intensity indicate the presence of regions of corrosion. In the other case a set of coils connected in a bridge circuit is used to induce eddy currents in the pipe wall. The presence of faults is indicated by out-of-balance signals.

A major problem is to maintain the sensors in close proximity with the pipe wall as the pig traverses girth welds, bends and like obstructions. The usual solution to this problem is to mount serveral sensors on a large heavy shoe mounted on a parallelogram link which is, in turn, mounted on the body of the pig by means of springs which urge the shoe into the desired position to the wall. Such shoes are, however, cumbersome and only partially effective. A better solution to the problem is desirable.

According to the invention there is provided a pig having at least one driving elastomeric cup member which is reacted upon by the pressure of the fluid flowing in a pipeline, wherein the improvement comprises at least one further elastomeric cup mounted upon the pig, the cup being an annular ring of elastomeric material having a shaped inner ring for fixing on to a pig body, a lip portion on the outer periphery of the ring which houses sensors for detecting defects in a pipeline, the sensors being mounted in the lip and standing proud of the outer surface of the lip, the sensors being urged radially outward from the inner ring by spring members fixed to the cup close to the inner ring and extending close to the sensors, the cup so arranged that when the pig is located in a pipeline the sensors are in slidable contact with the internal surface of the pipe.

Preferably the sensors mounted within the elastomeric cup are demountable from it so as to allow replacement of all or any of the sensors.

Preferably the sensors have a ceramic surface which is in contact with the internal surface of the pipe.

And further, it is preferable that the sensors can be made of an extended metal on their surface that is in contact with the internal surface of the pipe.

To enable the invention to be more clearly understood and solely by way of example one embodiment of the invention will be described with reference to the accompanying drawings, in which:

FIG. 1 is a side half sectional view of an elastomeric cup,

FIG. 2 is an end elevation of an elastomeric cup showing the sensors mounted thereon, FIG. 3 is a side elevational view of an elastomeric cup mounted upon a pig, and FIG. 4 is a side sectional elevation of a complete pig mounted within a pipeline showing the sensor mounting and driving cups.

With reference to the drawings the apparatus comprises a elastomeric cup seal 1 having sensors 2 fixed around its periphery. Around the inner periphery of the seal 1 are holes 3 for locating fixing means 4. Attached to the fixing means 4 is a leaf spring 5 provided with an end piece 6.

In use the elastomeric sensing cup is mounted upon the pig body 7, as shown in FIG. 4. Mounted in front of, and behind, the seal 1 are driving cups 8 and 9 which transmit the force of the flow of gas in the direction of the arrow A within the pipe 10 to the pig body and transmits the pig through the pipeline in the direction of the flow of gas. Whilst the pig is travelling through the pipeline the sensors 2 are forced against the internal surface 11 of the pipeline by the lead spring 5. The force from the leaf spring 5 is forced against the internal surface of the elastomeric seal 1 by means of an end piece 6 which is attached to the leaf spring 5 and projects partly around the circumference of the elastomeric seal 1. The leaf spring 5 is placed at required intervals around the seal 1 by means of the fixing holes 3. The sensors 2 transmit signals to the associated control circuitry attached to the pig and denote whether there are any imperfections in the pipe 10 wall.

An advantage of the invention is that the flexible elastomeric seal 1 slides over any obstruction in the internal wall of the pipe and can immediately flex back to its original position, thus maintaining the sensor 2 in contact with the internal surface 11 for as long a period as possible.

It is possible to locate more than one elastomeric seal containing sensors upon the pig body.

It is preferred to formulate the material of the flexible elastomeric seal so that variations in the bore of the pipe can be absorbed without buckling or distortion of the seal periphery.

The elastomeric seal may be rigidly fixed to the pig body, as illustrated in the accompanying drawings, or mounted on a movable ring. The movable ring is flexibly mounted on the pig body so that the flexible ring and elastomeric seal may move transversely with respect to the pig body when moving round a pipe bend.

I claim:

1. A pig having at least one driving elastomeric cup member which is reacted upon by the pressure of the fluid flowing in a pipeline, wherein the improvement comprises at least one further elastomeric cup mounted upon the pig, the cup being an annular ring of elastomeric material having an inner ring for fixing onto a pig body, a lip portion on the outer periphery of the ring which houses sensors for detecting defects in a pipeline, the sensors being mounted in the lip and being urged radially outward from the inner ring by spring members fixed to the cup close to the inner ring and extending close to the sensors, so arranged that when the pig is located in a pipeline the sensors are in slidable contact with the internal surface of the pipe.

2. A pig according to claim 1, wherein the sensors are removably mounted in the elastomeric cup.

3. A pig according to claim 1, wherein the sensors have a ceramic surface which is in sliding contact with the internal surface of the pipe.

4. A pig according to claim 1, wherein the sensors have an extended metal surface which is in contact with the internal surface of the pipe.

5. A cup for use on a pipeline comprising an annular ring of elastomeric material having an inner ring for fixing onto a pig body, a lip portion on the outer periphery of the ring which houses sensors for detecting defects in a pipeline, the sensors being mounted in the lip and being urged radially outward from the inner ring by spring members fixed to the cup close to the inner ring and extending close to the sensors, the cup so arranged that when the pig is located in a pipeline the sensors are in slidable contact with the internal surface of the pipe.

* * * * *

UNITED STATES PATENT OFFICE
CERTIFICATE OF CORRECTION

PATENT NO. : 4,098,126
DATED : July 4, 1978
INVENTOR(S) : David Campbell Howard

It is certified that error appears in the above-identified patent and that said Letters Patent are hereby corrected as shown below:

On the Title page of the patent, the following information should be added:

-- Foreign Application Priority Data

British Patent Application No. 13886/76, filed April 6, 1976. --

Signed and Sealed this

Nineteenth Day of December 1978

[SEAL]

Attest:

RUTH C. MASON
Attesting Officer

DONALD W. BANNER
Commissioner of Patents and Trademarks